US012765907B2

(12) United States Patent
Nowosielski et al.

(10) Patent No.: US 12,765,907 B2
(45) Date of Patent: Oct. 20, 2026

(54) BIAXIAL CONTROLLER FOR A MINIMALLY INVASIVE SURGERY TOOL, A CAMERA FOR MINIMALLY INVASIVE SURGERY TRAINING AND A SYSTEM FOR MINIMALLY INVASIVE SURGERY TRAINING

(71) Applicant: Laparo Sp. Z o.o., Wrocław (PL)

(72) Inventors: Radoslaw Nowosielski, Opole (PL); Mateusz Rulewicz, Wrocław (PL); Melania Hofman, Wrocław (PL); Piotr Daroch, Wrocław (PL); Martyna Strauchmann, Wolsztyn (PL)

(73) Assignee: Laparo Sp. Z o.o., Wroclaw (PL)

( * ) Notice: Subject to any disclaimer, the term of this patent is extended or adjusted under 35 U.S.C. 154(b) by 261 days.

(21) Appl. No.: 18/261,129

(22) PCT Filed: Feb. 4, 2022

(86) PCT No.: PCT/IB2022/050985
§ 371 (c)(1),
(2) Date: Jul. 12, 2023

(87) PCT Pub. No.: WO2022/167990
PCT Pub. Date: Aug. 11, 2022

(65) Prior Publication Data
US 2024/0071254 A1 Feb. 29, 2024

(30) Foreign Application Priority Data
Feb. 8, 2021 (PL) ........................................ 436895

(51) Int. Cl.
*A61B 17/29* (2006.01)
*A61B 17/34* (2006.01)
*A61B 17/00* (2006.01)

(52) U.S. Cl.
CPC .............. *A61B 17/29* (2013.01); *A61B 17/34* (2013.01); *A61B 2017/00106* (2013.01)

(58) Field of Classification Search
CPC .................... A61B 17/29; A61B 17/34; A61B 2017/00106
See application file for complete search history.

(56) References Cited

U.S. PATENT DOCUMENTS

| | | | |
|---|---|---|---|
| 2011/0028992 A1 | 2/2011 | Geiger et al. | |
| 2017/0086927 A1 | 3/2017 | Auld et al. | |
| 2024/0268639 A1 * | 8/2024 | Nowosielski ...... | A61B 1/00183 |

FOREIGN PATENT DOCUMENTS

WO 2006002174 A2 1/2006

OTHER PUBLICATIONS

European Patent Office, International Search Report, Application No. PCT/IB2022/050985, Jul. 21, 2022, 4 Pages.

* cited by examiner

*Primary Examiner* — Robert P Bullington
(74) *Attorney, Agent, or Firm* — Ziegler IP Law Group, LLC.

(57) ABSTRACT

A biaxial controller for a minimally invasive surgery tool, a camera for minimally invasive surgery training and a system for minimally invasive surgery training. All the aspects of the disclosure are applicable during training surgeons for carrying out minimally invasive surgery procedures. The biaxial controller for the minimally invasive surgery tool includes a control arrangement, a computer connector, at least one tool connector, a first bearing coupled with a first arm which is coupled with a second bearing which is coupled with a second arm in which a trocar is positioned. In the trocar the minimally invasive surgery tool is accommodated that includes a sleeve and a handle. The camera for minimally invasive surgery training includes a sleeve, a handle, at least one sensor for measurement of the position of the minimally invasive surgery tool and a vision sensor positioned at the end of the sleeve, wherein the handle includes a focus adjustment knob and a sensor of rotation of the focus adjustment knob, wherein preferably the focus adjustment knob is seated on a third bearing which is positioned on a sleeve, and more preferably the third bearing is a ball bearing. The system for minimally invasive surgery training includes a housing, at least one tool socket, and in the at least one tool socket a biaxial controller is positioned, and a worktable.

29 Claims, 6 Drawing Sheets

Figure 1:
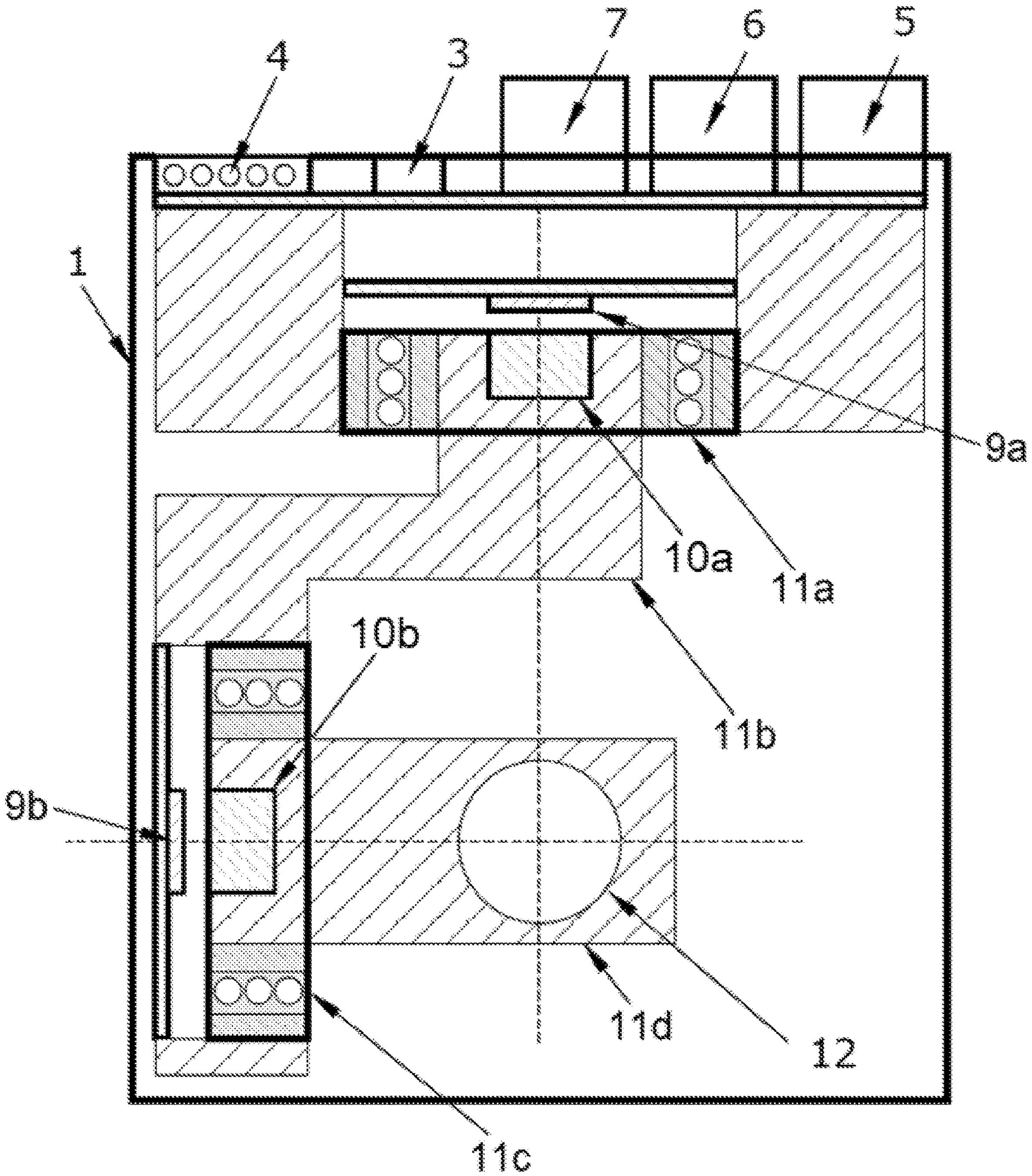

BIAXIAL CONTROLLER FOR A MINIMALLY INVASIVE SURGERY TOOL, A CAMERA FOR MINIMALLY INVASIVE SURGERY TRAINING AND A SYSTEM FOR MINIMALLY INVASIVE SURGERY TRAINING

The invention provides a biaxial controller for a minimally invasive surgery tool, a camera for minimally invasive surgery training and a system for minimally invasive surgery training. All the objects of the invention are applicable in training surgeons for performing minimally invasive surgery procedures.

Minimally invasive surgery training may be carried out, according to the solutions of the prior art, in two different environments: on physical objects or under virtual reality conditions. Each of the mentioned concepts has its advantages and disadvantages. The invention provides a complete solution that makes it possible to combine the two mentioned environments. This idea enables complete learning of the surgeon skills under the most suitable conditions. This hybrid solution maximizes advantages of the two solutions and eliminates shortcomings thereof. Physical trainer simulator is necessary to develop proficiency in manual skills. For example, sewing skill learning should be performed on real training objects. Virtual reality in turn helps in surgical procedures. Simulated environment very closely reflects the operation anatomy and teaches the user to use proper surgery operational technique step by step for each procedure type. Additionally, under the conditions of virtual reality the user may learn electrosurgery under safe conditions.

Document CN 2751372 Y discloses a training table with a laparoscope simulation, including a container for a casting of an abdomen, a camera and a monitor. The casting chamber of the abdominal cavity simulates an artificial condition of abdominal pneumatosis in a laparoscopic procedure. The camera is positioned within the container for the abdomen and is connected to the monitor. The surface of the box is provided with connecting openings wherein laparoscope operational instruments are placed. Simulated portions of the human body are positioned within the container.

Document CN 203038553 U discloses a training device for laparoscope simulation. The training device effectively integrates a body surface panel, a supporting panel, an operation platform, a base plate and a side panel by means of hinges, and it is capable of simulating the piercing channel in the human body surface and in a cavity in a human body. Simulation instruments may be introduced into the training device in order to carry out trainings in stitching technology, ligation and separation, that are used for the purpose of simulation of a surgery procedure area.

Document PL 424841 A1 discloses a handling/measuring member of a laparoscope training device that enables manual and virtual laparoscope training. A grip accommodates a sensor of opening of the operational tip jaw. From below the grip, in a sleeve axis, a flat light reflecting reflector is centrally secured. A trocar has a funnel-shaped body closed by a cover at the top, and within it there is an axially positioned guiding channel for an operational tool as well as sensors to determine desired parameters that characterize the action of the operational tool.

The invention provides a biaxial controller for a minimally invasive surgery tool, comprising a control arrangement, a computer connector and at least one tool connector for receiving signals from the minimally invasive surgery tool. A first bearing is engaged with a first arm which first arm is engaged with a second bearing. The second bearing is engaged with a second arm provided with an aperture. In the aperture there is a trocar that has a through hole in which a minimally invasive surgery tool is positioned. The minimally invasive surgery tool comprises a sleeve and a handle, and the biaxial controller also comprises a first sensor to determine the rotation angle of the first bearing and a second sensor to determine the rotation angle of the second bearing, and at least one sensor for measurement of the position of the minimally invasive surgery tool. The axes of the first bearing and the second bearing are crossed on the axis of the aperture.

Preferably, the biaxial controller is characterized in that the first sensor is a magnetic sensor and in the first arm a first magnet is provided.

Preferably, the biaxial controller is characterized in that the second sensor is a magnetic sensor and on the second arm a second magnet is provided.

Preferably, the biaxial controller is characterized in that the first bearing is a ball bearing.

Preferably, the biaxial controller is characterized in that the second bearing is s ball bearing.

Preferably, the biaxial controller is characterized in that that it comprises a trocar connector for receiving signals from the trocar.

Preferably, the biaxial controller is characterized in that the computer connector is a USB connector.

Preferably, the biaxial controller is characterized in that it comprises at least one sensor for determining the depth at which the minimally invasive surgery tool is inserted.

Preferably, the biaxial controller is characterized in that the sensor for determining the depth at which the minimally invasive surgery tool is inserted is a reflective sensor and a reflector.

Preferably, the biaxial controller is characterized in that the reflective sensor is an ultrasound sensor.

Preferably, the biaxial controller is characterized in that the reflective sensor is an optical sensor.

Preferably, the biaxial controller is characterized in that the reflective sensor is positioned on the trocar, and a reflector is positioned on the minimally invasive surgery tool.

Preferably, the biaxial controller is characterized in that the reflective sensor is positioned on the minimally invasive surgery tool, and the reflector is positioned on the trocar.

Preferably, the biaxial controller is characterized in that the sensor for determining the depth at which the minimally invasive surgery tool is inserted is a photosensitive matrix positioned in the trocar so that the photosensitive matrix faces the sleeve.

Preferably, the biaxial controller is characterized in that comprises position indication means.

Preferably, the biaxial controller is characterized in that the position indication means is a position connector.

Preferably, the position connector is connected to at least one passive element, preferably a resistor, or the position connector is connected to at least one semiconductor element, preferably with an integrated circuit.

Preferably, the position connector has means for reading position data.

Preferably, the biaxial controller is characterized in that the sensor for rotation measurement of the minimally invasive surgery tool is an accelerometer.

Preferably, the biaxial controller is characterized in that the axes of the first bearing and the second bearing cross in the aperture axis.

Preferably, the biaxial controller is characterized in that the minimally invasive surgery tool is a movement controller comprising a jaw.

Preferably, the biaxial controller is characterized in that the jaw comprises a movable jaw portion and an immovable jaw portion.

Preferably, the biaxial controller is characterized in that the jaw comprises two movable jaw portions.

Preferably, the biaxial controller is characterized in that the movement controller comprises a non-volatile memory.

Preferably, the biaxial controller is characterized in that it comprises a movable handle portion.

Preferably, the biaxial controller is characterized in that it comprises a handle opening sensor.

Preferably, the biaxial controller is characterized in that the handle opening sensor is a reflective sensor.

Preferably, the biaxial controller is characterized in that the handle opening sensor is an ultrasound sensor.

Preferably, the biaxial controller is characterized in that the handle opening sensor is an optical sensor.

A further invention is a camera for minimally invasive surgery training, comprising a sleeve, a handle and at least sensor for measurement of rotation of the minimally invasive surgery tool and a vision sensor positioned at the end of the sleeve. The handle comprises a focus adjustment knob seated in a third bearing which is positioned on the sleeve, more preferably, the third bearing is a ball bearing.

Preferably, the camera is characterized in that the sensor of the focus adjustment knob is a magnetic sensor.

Preferably, the camera is characterized in that the handle comprises a linking element and a sensor of vision path rotation. The sleeve is constituted by a first sleeve portion and a second sleeve portion. The linking element is seated in a fourth bearing, preferably the fourth bearing being a ball bearing. The fourth bearing is positioned on the first sleeve portion and the second sleeve portion is linked to the linking element. The second sleeve portion comprises a vision sensor. Preferably, the linking element comprises a guiding opening.

Preferably, the camera is characterized in that the sensor of the vision path rotation is a magnetic sensor.

Preferably, the camera is characterized in that the handle comprises at least one press button.

Preferably, the camera is characterized in that it comprises illumination at the vision sensor.

Preferably, the camera is characterized in that it comprises, within the optic path, an objective lens.

Preferably, the camera is characterized in that it comprises, within the optic path of the vision sensor, an electrically controlled lens.

Preferably, the camera is characterized in that the vision sensor is positioned on a base that is arranged on a movable extension arm.

Preferably, the camera is characterized in that the vision sensor is positioned on a base that is connected to an extension arm. The extension arm is engaged with the motor rotation axis by means of a transmission.

Preferably, the camera is characterized in that the vision sensor is positioned on a base rotationally connected to an immovable arm and a movable arm. The movable arm is connected to an extension arm engaged with the motor rotation axis with a transmission.

Preferably, the camera is characterized in that the vision sensor is positioned on a base rotationally connected to an immovable arm and a movable arm. The movable arm is connected to an extension arm engaged with the motor advance axis with a transmission.

Preferably, the camera is characterized in that the sensor for rotation measurement of the minimally invasive surgery tool is an accelerometer.

Preferably, the camera is characterized in that the camera is a minimally invasive surgery tool in a biaxial controller.

A further invention is a system for minimally invasive surgery training, comprising a housing, at least one tool socket, and preferably comprising a position connector, more preferably the position connector is connected to at least one passive element or a semiconductor element. In the at least one tool socket a biaxial controller is positioned. The system also comprises a worktable accommodated within the housing.

Preferably, the system is characterized in that the housing, in its interior, comprises at least one operation socket, preferably comprises three operation sockets. The worktable is attached to at least an operation socket.

Preferably, the system is characterized in that it comprises eight tool sockets.

Preferably, the system is characterized in that each of the tool sockets has a position connector.

The aim of the invention is to provide tools for minimally invasive surgery training, which combine advantages of the training in virtual reality and the training on a physical object.

Figure 2:
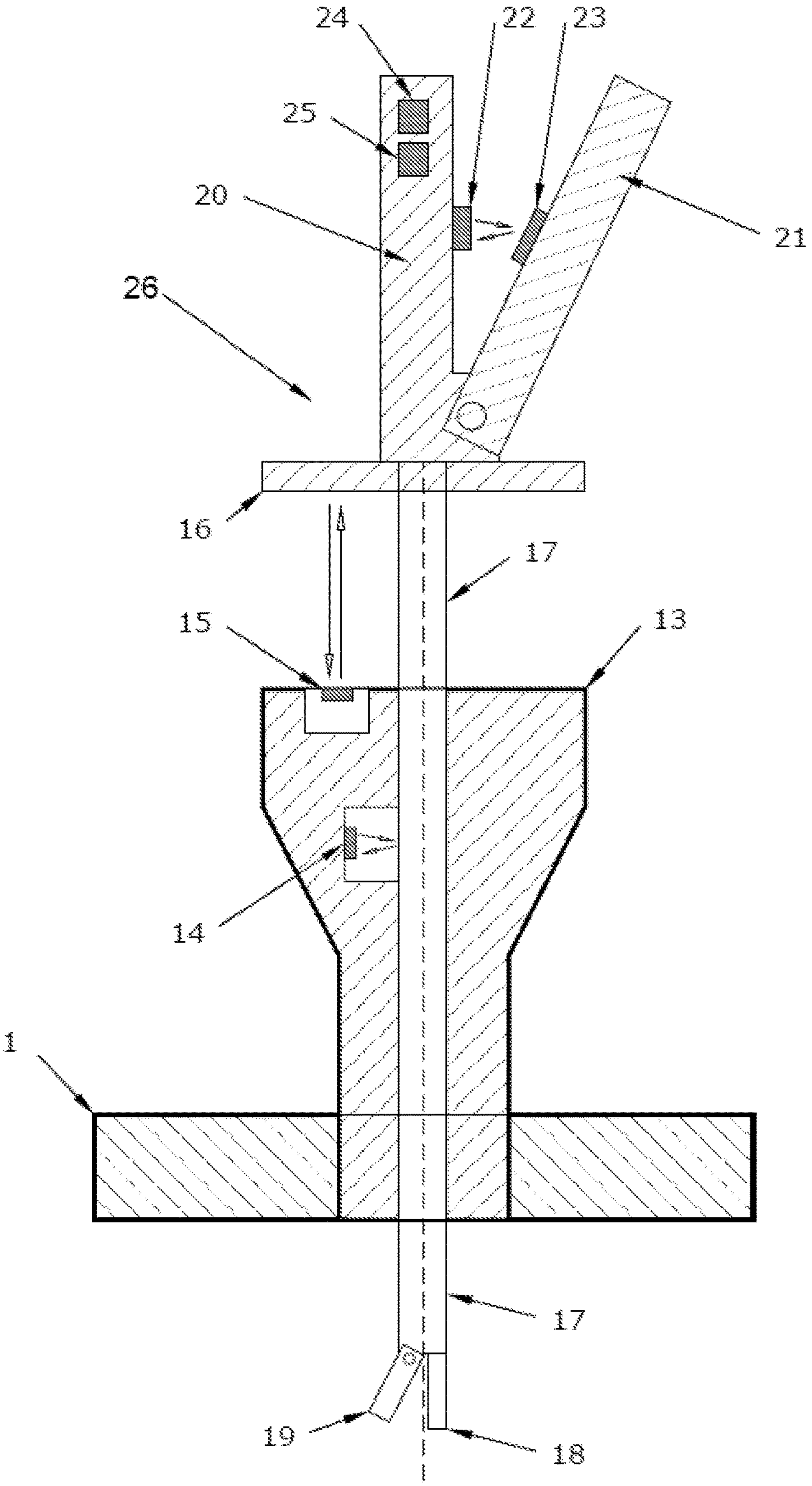
Figure 3:
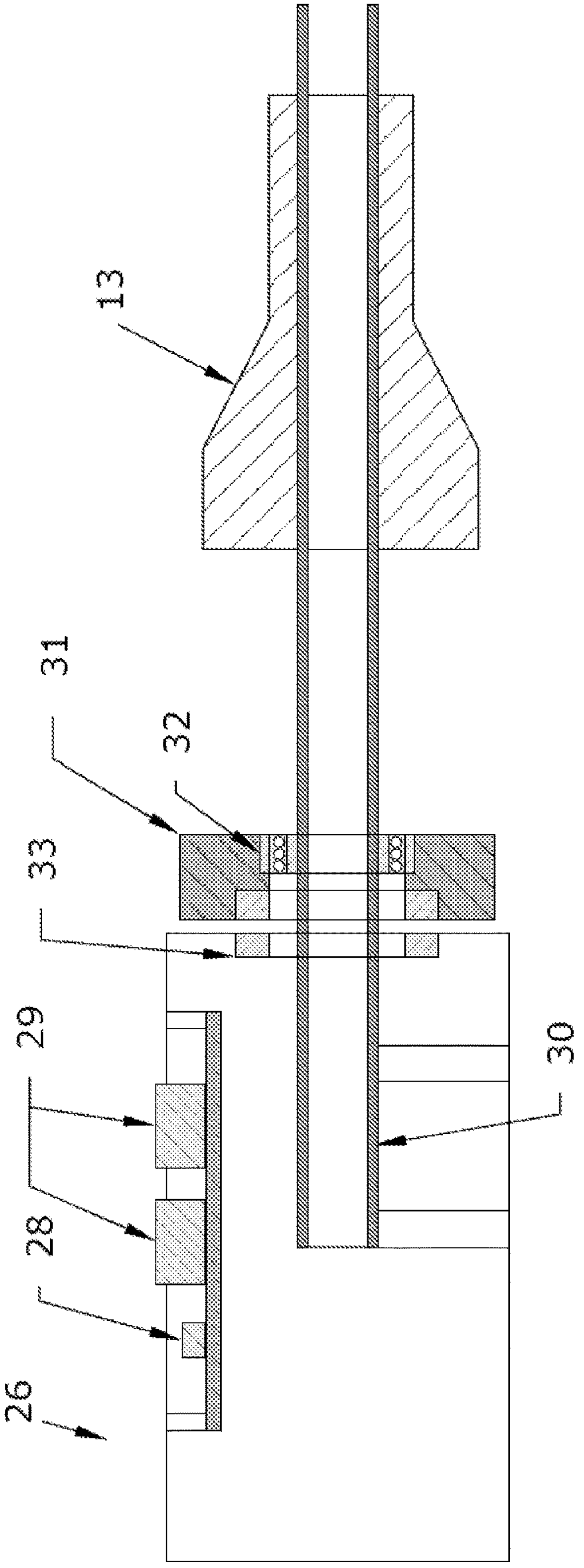
Figure 4:
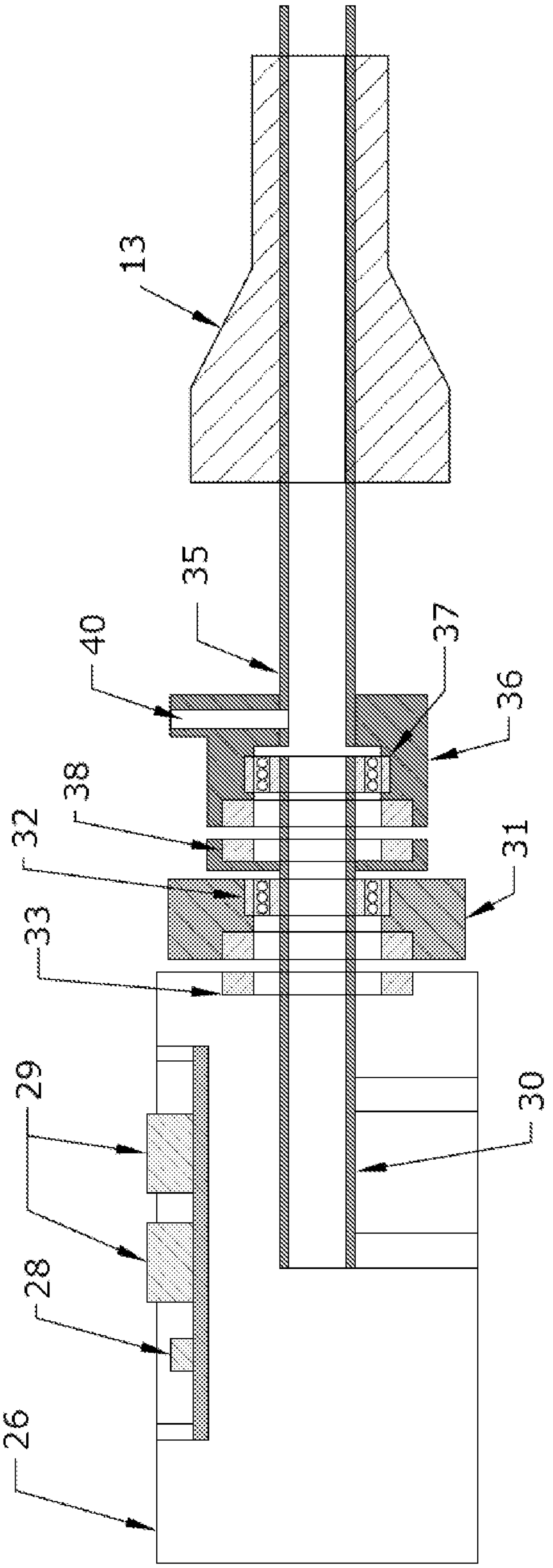
Figure 5:
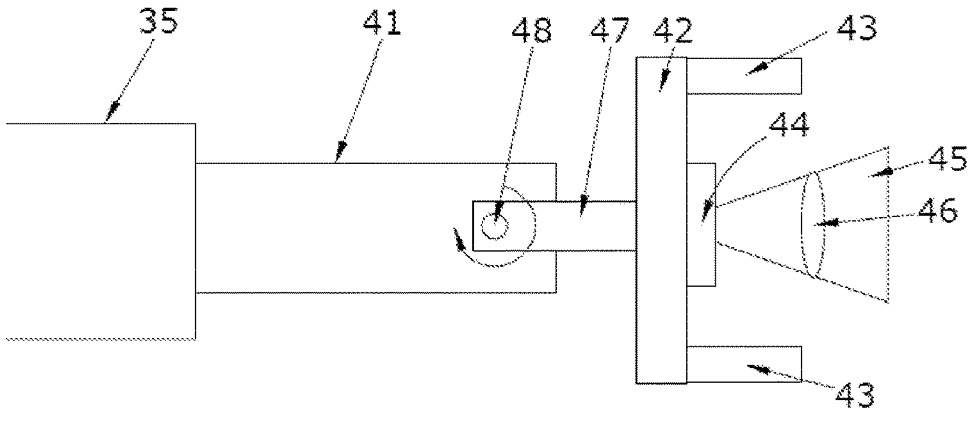
Figure 6:
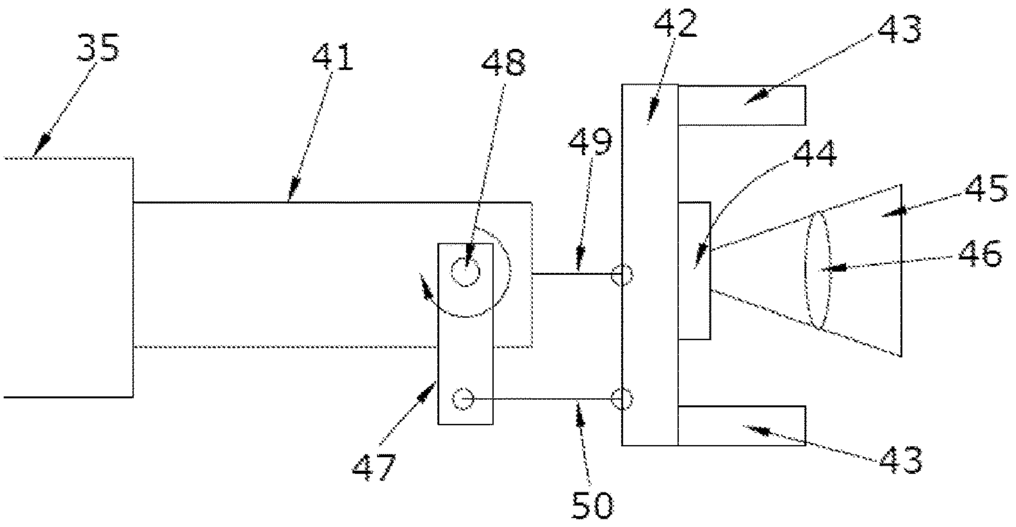
Figure 7:
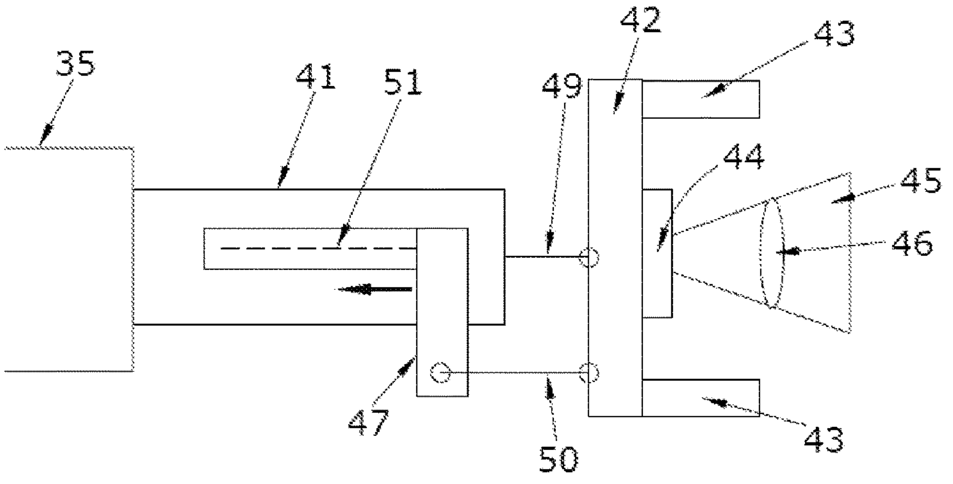
Figure 8:
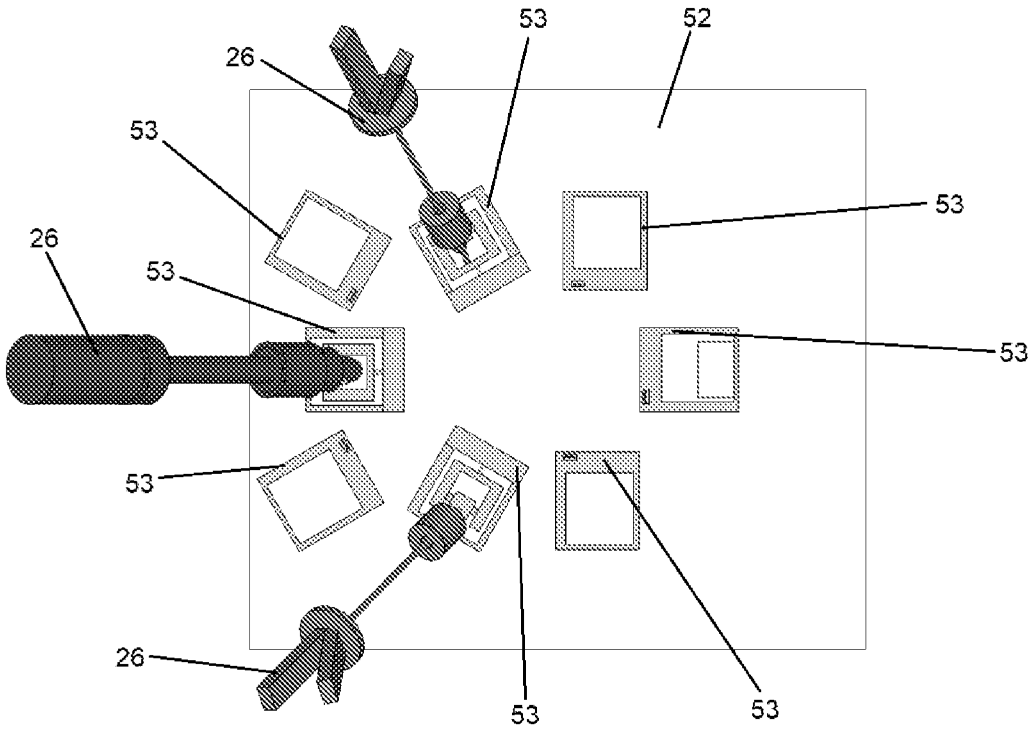
Figure 9:
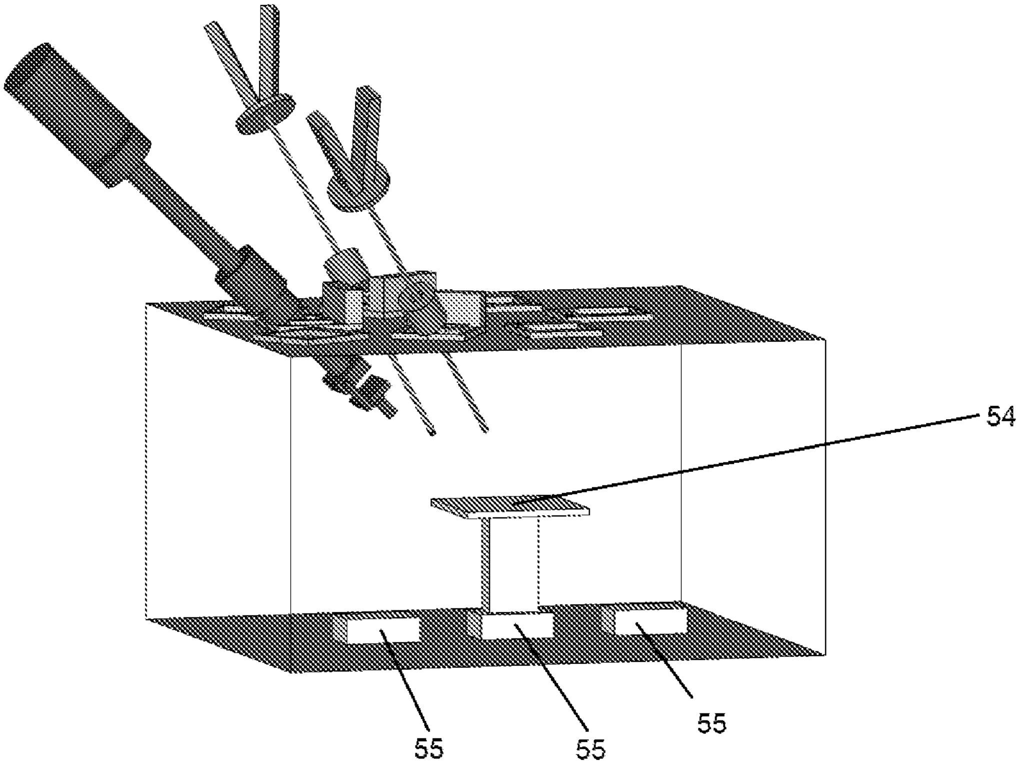

The inventions are presented in the figures of the drawing wherein:

FIG. 1 shows an embodiment of a biaxial controller,

FIG. 2 shows an exemplary minimally invasive surgery tool attached to a biaxial controller, FIG. 3-4 show embodiments of a handle of a camera for minimally invasive surgery training FIG. 5-7 show embodiments of a movable vision sensor in a camera for minimally invasive surgery training FIG. 8 shows a top view of a system for minimally invasive surgery training FIG. 9 shows an embodiment of a worktable in a system for minimally invasive surgery training.

[FIG. 1] shows a biaxial controller 1 for a minimally invasive surgery tool. The biaxial controller 1 comprises a control arrangement 3 which analyses operation of the device and reads data out of the sensors. Furthermore, it also comprises a computer connector 5, preferably a USB connector, for communication with a computer, at least one tool connector 7 for receiving signals from the minimally invasive surgery tool 26. To the housing of the device, directly or indirectly, a first bearing 11*a* is attached which is engaged with a first arm 11*b* which first arm 11*b* is engaged with a second bearing 11*c* which is engaged with a second arm 11*d* in which an aperture 12 is provided in which a trocar 13 is positioned that comprises a through hole in which the minimally invasive surgery tool 26 is positioned the exemplary embodiment of which is shown in [FIG. 2]. This connection of movable elements enables rotation of the minimally invasive surgery tool 26 such as during a surgery procedure—the rotation point is fixed in the biaxial controller 1, and the biaxial controller 1 simulates the position of introduction of the minimally invasive surgery tool 26 into the body of the patient. The tool 26 as such comprises a sleeve 17 at the end of which varied tips may be arranged, e.g., claws or a camera, and a handle 20. The biaxial controller 1 also comprises a first sensor 9*a* for determining rotation angle of the first bearing 11*a* and a second sensor 9*b* for determining rotation angle of the second bearing 11*c*, and at least one sensor for position measurement of the minimally invasive surgery tool 26. Furthermore, the axes of the first bearing 11*a* and the second bearing 12*c* cross in the axis of the aperture 12, preferably they cross in the axis of the aperture 12.

In a preferable embodiment, the first sensor 9*a* is a magnetic sensor, and in the first arm 11*b* a first magnet 10*a* is arranged. Furthermore, the second sensor 9*b* may be also a magnetic sensor, and then in the second arm 11*d* a second magnet 10*b* is arranged.

In a further embodiment, the first bearing 11*a* is a ball bearing. The second bearing 11*b* is a ball bearing.

In another embodiment, the biaxial controller 1 comprises a trocar connector 6 for receiving signals from the trocar 13, and more precisely, for receiving information from the sensors provided in the trocar 13.

In a yet another embodiment, biaxial controller 1 comprises at least one sensor for determining the depth at which the minimally invasive surgery tool 26 is inserted, being an exemplary sensor for measuring the position of the minimally invasive surgery tool 26. This sensor enables precise determining of the position of the device and simulating operations in the virtual reality. The depth sensor may be for example a reflective sensor 15 that cooperates with a reflector 16. One of these elements is positioned in the trocar 13, while the other one is positioned in the handle 20. the reflective sensor 15 may be for example an ultrasound sensor or an optic sensor. Another solution is the use of a photosensitive matrix 14 positioned in the trocar 13 so that the photosensitive matrix 14 faces the sleeve 17. The photosensitive matrix 14 takes photographs of the surface of the sleeve 17 and compares changes in the subsequent photographs and this makes it possible to determine the change in the advancement position of the sleeve and its axial rotation. In a preferable embodiment there are two kinds of sensors, i.e. a reflective sensor 15 and a photosensitive matrix 14. In this configuration the device may quickly determine the depth at which the tool 26 is inserted by means of the photosensitive matrix 14, and the changes are defined absolutely by the reflective sensor 15. It should be noted that other solutions enabling precise changes in the position, e.g. linear encoder, may be used instead as it will be apparent for a person skilled in the art.

As shown in [FIG. 8], biaxial controller 1 cooperates with the housing 52 of a system for minimally invasive surgery training. In a preferable embodiment, the biaxial controller 1 has position indication means, i.e., means for transmitting to the computer of information in which socket 53 the biaxial controller 1 is mounted. Absence of such means implies an obligation for the use to introduce manually the respective data to the computer. In a preferable embodiment the position indication means is a position connector 4. The position connector 4 may comprise at least one passive element, preferably a resistor, or at least one semiconductor element, preferably an integrated circuit. It should be noted that any combination of passive and active elements is allowable, and the specific solution will be apparent for a person skilled in the art. In another variety, the position connector 4 has means for reading out position data—these means make it possible to determine to which tool socket 53 the biaxial controller is connected. Dependently on the element used in the tool socket 53 (resistor, integrated circuit, etc.), the data readout and this the means for data readout will be different, but a person skilled in the art will be able to select suitable means for detection of position of the biaxial controller.

In another embodiment of biaxial controller 1, the sensor for rotation measurement of 26 is an accelerometer 24. The accelerometer is used mainly for absolute determining the rotation angle of the tool 26, but a person skilled in the art will be able, when needed, to obtain information concerning changes in the position of the tool 26.

In another embodiment, the minimally invasive surgery tool 26 is a movement controller comprising a jaw. The jaw may comprise a movable jaw portion 19 and an immovable jaw portion 18, but it may also comprise two movable jaw portions 19. Preferably, biaxial controller 1 may also include a movable portion 21 of the handle 20, and it can further comprise a sensor 22 of handle opening. The handle opening sensor 22 may be a reflective sensor, e.g. an ultrasound sensor or an optic sensor. Such a solution enables a combined training, where a part of the training is simulated by the computer, and the user may train, e.g. stitching or knotting on a real object. Physical interaction between such object better reproduces real conditions for computer simulation and this enables achieving better training results.

Preferably, biaxial controller 1 comprises a non-volatile memory 25.

FIGS. 3-7 show embodiments of a camera for minimally invasive surgery training. The camera comprises a sleeve 17, a handle 20, at least one sensor for measuring rotation of the minimally invasive surgery tool 26 and a vision sensor 44 positioned at the end of the sleeve 17. The handle comprises a knob 31 for focus adjustment and a sensor 33 of rotation of the focus adjustment knob 31, and preferably also at least one press button 29. Preferably, the focus adjustment knob 31 is seated in a third bearing 32 which is positioned on the sleeve 17, and more preferably the third bearing 32 is a ball bearing. Preferably, the sensor 33 of rotation of the focus adjustment knob 31 is a magnetic sensor. This construction enables reproduction of work on a real tool that would be used in a surgery procedure while the cost and requirements for the camera for training are lower than the ones related to the optic path used during the actual surgery procedure.

In a preferable embodiment, the handle 20 comprises a linking element 36 and a sensor 38 of rotation of the vision path. The sleeve 17 in this embodiment is constituted by a first portion 30 of the sleeve 17 and a second sleeve portion 35. The linking element 36 is seated on a fourth bearing 37, preferably the fourth bearing 37 being a ball bearing positioned on the first portion 30 of the sleeve 17, while the second portion 35 of the sleeve 17 is linked with the linking element 36. The second portion 35 of the sleeve 17 comprises a vision sensor 44. Preferably, the linking element 36 comprises a guiding hole 40.

The camera may be provided with additional equipment to enhance video reception, for example the camera may comprise illumination 43 at the vision sensor 44, an object lens 45, in the optic path of the vision sensor 44, and a lens 46 electrically controlled, within the optic path of the vision sensor 44. A person skilled in the art will be aware which of these elements are necessary for carrying out of the invention in a specific case.

Preferably, the vision sensor 44 may be set at different angles and this enables reproduction of operation of real vision paths during surgery procedures. The camera may achieve this aim by means of diverse mechanisms, where for example the vision sensor 44 is positioned on a base 42, which base is positioned on a movable extension arm 47, or the vision sensor 44 is positioned on a base 42 which is engaged with an extension arm 47 and the extension arm 47 is engaged with the rotation axis 48 of a motor 41 with a transmission. Furthermore, the vision sensor 44 may be positioned on a base 42 rotationally coupled with an immovable arm 49 and a movable arm 50, and the movable arm 50 is coupled with an extension arm 47 engaged with the rotation axis 48 of a motor 41 with a transmission. In another example the vision sensor 44 is positioned on a base 42 rotationally engaged with an immovable arm 49 and a movable arm 50, and the movable arm 50 is engaged with an extension arm 47 engaged with the advancement axis 51 of a motor 41 with a transmission.

In a preferable embodiment, the camera is provided with an accelerometer 28 which may be positioned for example in the handle 20 or in the linking element 36. Also preferably, the camera may be positioned in the biaxial controller 1, where it functions as the minimally invasive surgery tool 26.

It should be noted that in FIGS. 5-7 the second sleeve portion 35 may be replaced, suitably to the variant contemplated, by the sleeve 17.

FIGS. 8-10 show a system for minimally invasive surgery training, comprising a housing 52 and at least one tool socket 53, preferably eight of them. The tool socket 53 may comprise a position connector 4. For example, a position connector 4 is connected to at least one passive element or semiconductor element, and this enables identification of the biaxial controller inserted into the socket. It should be emphasized that also a variant is contemplated in which the system reads out the position of the biaxial controller. In at least one tool socket 53 there is a biaxial controller 1 such as described above. Additionally, the system has a worktable 54. The system provides fixed mounting points for the tools 26 secured in biaxial controllers 1, and this enables providing simulation for standard positions of tools 26. Additionally, the worktable 54 enables providing a physical object. In a system thus prepared is to simulate virtually a surgery procedure, where the stitching operation is performed by physical action on the object.

In a preferable embodiment, the system comprises at least one operation socket 55, and preferably it comprises three operation sockets 55. The operation sockets 55 enable shifting the worktable 54, and this enables arranging a larger number of exercises on the same workstation as shown in [FIG. 9]. The operation sockets 55 are positioned within the housing 52.

In a preferable embodiment, each of the tool sockets 53 has a position connector 4 which cooperates with the position connector 4 in the biaxial controller 1.

It should be noted that all the connectors are meant as means for transmitting or receiving signals. This may be effected both in a wired manner and wirelessly.

1 biaxial controller
3 control arrangement
4 position connector
5 computer connector
6 trocar connector
7 tool connector
9*a* first sensor
9*b* second sensor
10*a* first magnet
10*b* second magnet
11*a* first bearing
11*b* first arm
11*c* second bearing
11*d* second arm
12 aperture
13 trocar
14 photosensitive matrix
15 reflective sensor
16 reflector
17 sleeve
18 immovable jaw portion
19 movable jaw portion
20 handle
21 movable handle portion.
22 handle opening sensor
24, 28 accelerometer
25 non-volatile memory
26 minimally invasive surgery tool
29 press button
30 first sleeve portion
31 focus adjustment knob
32 third bearing
33 focus adjustment knob sensor
35 second sleeve portion
36 linking element
37 fourth bearing
38 sensor of rotation of the vision path
40 guiding hole
41 motor with a transmission
42 base
43 illumination
44 vision sensor
45 object lens
46 movable lens
47 extension arm
48 rotation axis
49 immovable arm
50 movable arm
51 advancement axis
52 housing
53 tool socket
54 worktable
55 operation socket

The invention claimed is:

1. A biaxial controller for a minimally invasive surgery tool, comprising a controlling arrangement, a computer connector, at least one tool connector for receiving signals from the minimally invasive surgery tool and a first bearing engaged with a first arm, which first arm is engaged with a second bearing which is engaged with a second arm in which an aperture is arranged in which a trocar is positioned comprising a through hole in which invasive surgery tool is arranged that comprises a sleeve and a handle, and the biaxial controller also comprises a first sensor for determining rotation angle of the first bearing and a second sensor for determining rotation angle of a second bearing, and at least one sensor for measurement of the position of the minimally invasive surgery tool, where the axes of the first bearing and the second bearing cross in the axis of the aperture.

2. The biaxial controller according to claim 1 wherein the first sensor is a magnetic sensor, and in the first arm a first magnet is arranged.

3. The biaxial controller according to claim 1 wherein the second sensor is a magnetic sensor, and in the second arm a second magnet is arranged.

4. The biaxial controller according to claim 1, wherein the first bearing is a ball bearing.

5. The biaxial controller according to claim 1, wherein the second bearing is a ball bearing.

6. The biaxial controller according to claim 1, wherein it comprises a trocar connector for receiving signals from the trocar.

7. The biaxial controller according to claim 1, wherein the computer connector is a USB connector.

8. The biaxial controller according to claim 1, wherein it comprises at least one sensor for determining the depth at which the minimally invasive surgery tool is inserted.

9. The biaxial controller according to claim 8 wherein the sensor for determining the depth at which the minimally invasive surgery tool is inserted is a reflective sensor and a reflector.

10. The biaxial controller according to claim 9 wherein the reflective sensor is an ultrasound sensor.

11. The biaxial controller according to claim 9 wherein the reflective sensor is an optical sensor.

12. The biaxial controller according to claim 9, wherein the reflective sensor is positioned on the trocar, and the reflector is positioned on the minimally invasive surgery tool.

13. The biaxial controller according to claim 9, wherein the reflective sensor is positioned on the minimally invasive surgery tool, and the reflector is positioned on the trocar.

14. The biaxial controller according to claim 8, wherein the sensor for determining the depth at which the minimally invasive surgery tool is inserted is a photosensitive matrix positioned in the trocar so that the photosensitive matrix faces the sleeve.

15. The biaxial controller according to claim 1, wherein it comprises position indication means.

16. The biaxial controller according to claim 15, wherein the position indication means is a position connector.

17. The biaxial controller according to claim 16, wherein the position connector is connected to at least one passive element, preferably a resistor, or the position connector is connected to at least one semiconductor element, preferably an integrated circuit.

18. The biaxial controller according to claim 16, wherein the position connector has means for reading out position data.

19. The biaxial controller according to claim 1, wherein the sensor for measurement of rotation of the minimally invasive surgery tool is an accelerometer.

20. The biaxial controller according to claim 1, wherein the axes of the first bearing and the second bearing cross in the axis of the aperture.

21. The biaxial controller according to claim 1, wherein the minimally invasive surgery tool is a movement controller comprising a jaw.

22. The biaxial controller according to claim 21, wherein the jaw comprises a movable jaw portion and an immovable jaw portion.

23. The biaxial controller according to claim 21, wherein the jaw comprises two movable jaw portions.

24. The biaxial controller according to claim 21, wherein the movement controller comprises a non-volatile memory.

25. The biaxial controller according to claim 21, wherein it comprises a movable portion of the handle.

26. The biaxial controller according to claim 25, comprising a sensor of a handle opening.

27. The biaxial controller according to claim 26, wherein the handle opening sensor is a reflective sensor.

28. The biaxial controller according to claim 27, wherein the handle opening sensor is an ultrasound sensor.

29. The biaxial controller according to claim 27, wherein the handle opening sensor is an optical sensor.

* * * * *